United States Patent [19]

Matsuoka et al.

[11] Patent Number: 5,179,013
[45] Date of Patent: * Jan. 12, 1993

[54] CYTOCHROME P-450 ENZYMES

[75] Inventors: Tatsuji Matsuoka; Shunichi Miyakoshi, both of Hiromachi, Japan

[73] Assignee: Sankyo Company, Limited, Tokyo, Japan

[*] Notice: The portion of the term of this patent subsequent to Oct. 6, 2009 has been disclaimed.

[21] Appl. No.: 532,101

[22] Filed: May 30, 1990

Related U.S. Application Data

[63] Continuation of Ser. No. 150,013, Jan. 29, 1988, abandoned.

[30] Foreign Application Priority Data

Feb. 2, 1987 [JP] Japan .................... 62-21954
Aug. 26, 1987 [JP] Japan .................... 62-210217

[51] Int. Cl.$^5$ .................... C12P 17/06; C12N 9/02
[52] U.S. Cl. .................... 435/125; 435/189; 435/191; 530/401
[58] Field of Search .................... 435/191, 189, 886, 125, 435/119, 135; 530/401

[56] References Cited

FOREIGN PATENT DOCUMENTS 0215665 3/1987 European Pat. Off. .

OTHER PUBLICATIONS

Sarialani, F. S. et al. (1986) Biochem. Biophys. Res. Commun. 141(2), 405-410.
Shafiee, A. et al. (1987) Biochemistry 26, 6204-6210.
Corcoran, J. W., et al. (1982) Biochemistry 21, 263-269.
Serizawa, N. et al. (1983) J. of Antibiotics 36 (5), 604-607 and 608-610.
Michael K. Trower et al., 1989, pp. 1781-1787 Purification and Characterization of a Soybean Flour-Induced Cytochrome P-450 from *Streptomyces griseus*, vol. 171 Journal of Bacteriology.

Primary Examiner—Charles L. Patterson, Jr.
Attorney, Agent, or Firm—Frishauf, Holtz, Goodman & Woodward

[57] ABSTRACT

Novel cytochrome P-450$_{sca-1}$, P-450$_{sca-2}$ and P-450$_{sca-3}$ enzymes are produced by cultivation of *Streptomyces carbophilus* SANK 62585, and are suitable for use in hydroxylation processes.

17 Claims, No Drawings

CYTOCHROME P-450 ENZYMES

This application is a continuation of application Ser. No. 150,013, filed Jan. 29, 1988, now abandoned.

BACKGROUND OF THE PRESENT INVENTION

The present invention relates to novel cytochrome P-450 enzymes.

The enzyme cytochrome P-450 has been found in animals, plants, and microorganisms. The cytochrome P450-dependent monooxygenase system catalyses the biosynthesis of important physiological compounds, and participates in the metabolism of foreign substances, xenobiotics. It can use as a substrate a wide range of natural products and drugs.

For its enzymatic action, cytochrome P-450 requires a coenzyme such as MAD(P)H, an electron-transport protein such as ferredoxin, and molecular oxygen. The following mechanism is postulated for metabolism of a substrate S to give a product SOH, with Fe indicating the active site of the cytochrome P-450:

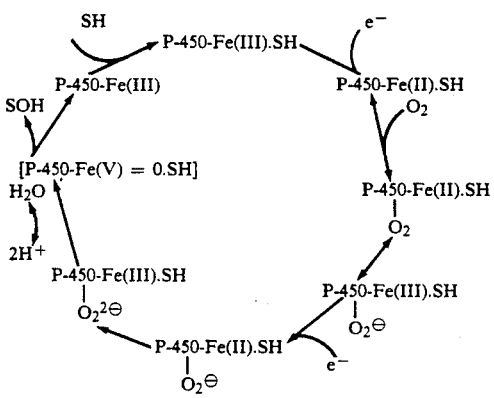

In this mechanism, the electrons which effect reduction are provided from AND(P)H through the mediating effect of the electron-transport protein.

In general, cytochrome P-450 enzymes have mainly been isolated from eucaryotes, and are insoluble in water.

Cytochrome P-450 enzymes isolated from procaryotes are also known, including P-450$_{cam}$ from *Pseudomonas putida* [J Biol Chem (1974) 249, 94]; P-450$_{BM-1}$ and P-450$_{BM-3}$ both from *Bacillus megaterium* ATCC 14581 [reported respectively in Biochim Hiophys Acta (1985) 838, 302 and J Biol Chem (1986) 261, 1986, 7160]; P-450a, P-450b, and P-450c from *Rhizobium japonicum* [Biochim Biophys Acta (1967) 147, 399]: and P-450$_{npd}$ from Nocardia NHI [Microbios (1974) 9, 119].

Cytochrome P-450 enzymes purified from Streptomyces microorganisms remain relatively unreported. The induction of a cytochrome P-450 in *Streptomyces griseus* by soybean flour is described in Biochem and Biophys Res Comm (1986) 141, 405. The isolation and properties of two forms of a 6-deoxyerythronolide B hydroxylase from *Saccharopolyspora erythraea* (originally classified as *Streptomyces erythraeus*) is described in Biochemistry (1987) 26, 6204.

In European Patent Specification 215,665 published on Mar. 25, 1987 and in corresponding U.S. Ser. No. 07/393,001, Aug. 11, 1989, which is a continuation of U.S. Ser. No. 07/203,649, Jun. 1, 1988, which is a continuation of U.S. Ser. No. 06/906,034 filed Sep. 10, 1986, there is described an enzymatic hydroxylation. Hydroxylation is effected with a hydroxylation enzyme produced by a microorganism of the genus Streptomyces or of the genus Nocardia.

Four newly isolated strains of Streptomyces which produce suitable hydroxylation enzymes are described in EP 215,665 and U.S. Ser. No. 07/393,001, which is a continuation of U.S. Ser. No. 07/203,649, which is a continuation of U.S. Ser. No. 06/906,034, including Streptomyces sp SANK 62585.

Streptomyces sp SANK 62585 was deposited with the Fermentation Research Institute, Japan, on Sep. 5, 1985 under the accession number FERM P-8440, and re-deposited under the Budapest Treaty on Aug. 13, 1986 under the accession number FERM BP-1145.

OBJECTS OF THE PRESENT INVENTION

It is an object of the present invention to provide novel cytochrome P-450 enzymes. It is also an object of this invention to provide a novel method for producing cytochrome P-450 enzymes, and processes for preparing hydroxylated compounds employing such enzymes.

SUMMARY OF THE PRESENT INVENTION

The present invention provides novel cytochrome P-450 enzymes. Such enzymes typically have a molecular weight of 46,000±1,000. The enzymes are obtained from Streptomyces, and are hydroxylation enzymes capable of hydroxylating a variety of different compounds.

PREFERRED EMBODIMENTS OF THE PRESENT INVENTION

Specifically, the present invention provides the novel enzymes cytochome P-450$_{sca-1}$, P-450$_{sca-2}$ and P-450$_{sca-3}$. When one or more of these enzymes is combined with suitable components to give an effective system, it can convert a substrate for the enzyme to a hydroxylated derivative.

The enzymes cytochrome P-450$_{sca-1}$, cytochrome P-450$_{sca-2}$, and/or cytochrome P-450$_{sca-3}$ can be extracted and purified from the known Streptomyces SANK 2585 FERM BP-1145 now identified as being of the species *Streptomyces carbophilus*.

As described in EP 215,665 and U.S. Ser. No. 07/393,001, which is a continuation of U.S. Ser. No. 07/203,649, which is a continuation of U.S. Ser. No. 06/906,034, the Streptomyces strain SANK 62585 was known to belong to the genus Streptomyces of the Actinomycetes. The reader is referred to the EP 215,665 and U.S. Ser. No. 06/906,034, incorporated herein by reference.

The morphological and physiological properties for Streptomyces strain SANK 62585 were determined using conventional media and the methods described by Shirling and Gottlieb [International Journal of Systematic Bacteriology (1966) 16, 313–340], together with several supplementary tests. Observations of the culture were made after incubation at 28° C. for 14 days. The colour names used were assigned according to the "Guide to Colour Standard" (a manual published by Nippon Shikisai Kenkyusho, Tokyo, Japan). The characteristics of the cultures were compared with those of various known species of actinomycetes described according to the ISP (International Streptomyces Project) standards and in "The Actinomycetes, Volume 2" by Waksman, "The ISP Report" by Shirling and Gottlieb, "Bergey's Manual of Determinative Bacteriology", 8th edition, and other recent literature concerning the taxonomy of the actinomycetes.

1. Morphological Properties

When observed under a microscope and under an electron microscope, the vegetative hyphae of strain SANK 62585 were fully developed with branching, and the aerial hyphae were monopodially branched.

The spore chain of strain SANK 62585 is usually straight or flexuous, but sometimes spiral and the spore surfaces are smooth. No special organs, such as whirls, sclerotia, basal hyphae fragmentation and sporangia, can be observed on SANK 62585.

2. Growth on Taxanomic Media

The growth of the strain on various media is shown in the next Table, where the following abbreviations are used:

| Medium | Item | G: growth<br>AM: aerial mycelium<br>R: reverse<br>SP: soluble pigment.<br>Property of Strain SANK 62585 |
|---|---|---|
| Sucrose nitrate agar | G | Not so good, pale yellowish orange (2-9-9) |
| | AM | Normal, powdery, greyish white (N-9) |
| | R | Pale yellowish orange (2-9-9) |
| | SP | None |
| Glucose/ asparagine agar | G | Not so good, yellowish grey to brownish grey [(2-5-9) to (1-9-10)] |
| | AM | Trace, greyish white (N-9) |
| | R | Yellowish grey to brownish grey [(2-5-9) to (1-9-10)] |
| | SP | None |
| Glycerin/ asparagine agar (ISP 5) | G | Not so good, pale yellowish brown (2-7-9) |
| | AM | Normal, powdery greyish white (N-9) |
| | R | Pale yellowish brown (4-8-9) |
| | SP | None |
| Starch/ inorganic salt agar (ISP 4) | G | Very good, brownish grey (2-6-9) |
| | AM | Abundant, powdery, yellowish grey to bright olive-grey [(1-9-10) to (2-8-12)] |
| | R | Pale brown to brownish grey [(2-8-9) to (2-4-9)] |
| | SP | None |
| Tyrosine agar (ISP 7) | G | Good, dark yellowish brown (4-4-9) |
| | AM | Very abundant, powdery, yellowish grey to bright olive-grey [(1-9-10) to (2-8-11)] |
| | R | Dark brownish grey (2-3-9) |
| | SP | None |
| Peptone yeast-iron agar (ISP 6) | G | Good, yellowish brown (4-6-9) |
| | AM | None |
| | R | Yellowish brown (4-6-9) |
| | SP | None |
| Nutrient agar (Difco) | G | Not so good, bright olive-grey (4-8-10) |
| | AM | None |
| | R | Bright olive-grey (4-8-10) |
| | SP | None |
| Yeast- malt agar olive- (ISP 2) | G | Very good, yellowish brown (6-7-9) |
| | AM | Very abundant, powdery, bright grey (2-8-11) |
| | R | Yellowish brown (6-5-9) |
| | SP | None |
| Oatmeal agar (ISP 3) olive- | G | Very good, greyish yellow brown (4-5-9) |
| | AM | Very abundant, powdery, bright grey (2-8-12) |
| | R | Dark brownish grey (2-3-9) |
| | SP | None |
| Potato/ carrot extract orange agar | G | Poor, yellowish grey to dull orange [(1-9-10) to (6-8-6)] |
| | AM | Normal, powdery, pale yellowish (2-9-9) |
| | R | Pale brown (3-8-6) |

| Medium | Item | G: growth<br>AM: aerial mycelium<br>R: reverse<br>SP: soluble pigment.<br>Property of Strain SANK 62585 |
|---|---|---|
| | SP | None |

3. Physiological Properties

The physiological properties of strain SANK 62585 are shown in the next table, wherein the media identified as Media 1 to 4 are:
Medium 1: Yeast extract Malt extract agar (ISP 2)
Medium 2: Tryptone Yeast extract Broth (ISP 1)
Medium 3: Peptone Yeast extract Iron agar (ISP 6)
Medium 4: Tyrosine agar (ISP 7)

| Properties of Strain SANK 62585 | |
|---|---|
| Hydrolysis of starch | positive |
| Liquefaction of gelatin | negative |
| Reduction of nitrate | positive |
| Coagulation of milk | positive |
| Peptonization of milk | positive |
| Temperature range for growth (Medium 1) | 4–45° C. |
| Optimum temperature for growth (Medium 1) | 15–33° C. |
| Melanoid formation (Medium 2) | negative |
| (Medium 3) | pseudopositive* |
| (Medium 4) | doubtful |

*pseudopositive: some instances occur of melanin formation towards the end of culturing By using Pridham-Gottlieb agar, the assimilation of various carbon sources after cultivation for 14 days was investigated. Since the strain SANK 62585 grows well on such control media without a carbon source, it is difficult to assess the exact assimilation capacity. Accordingly, the next following table shows, for the relative assimilation capacity of the strain on a reference control medium (i.e. an assessment of the difference in growth between control media with and without the added carbon source).

| Carbon Assimilation | |
|---|---|
| D-Glucose | utilized |
| L-Arabinose | not utilized |
| D-Xylose | utilized |
| Inositol | utilized |
| D-Mannitol | not utilized |
| D-Fructose | not utilized |
| Sucrose | not utilized |
| Raffinose | utilized |
| Cellobiose | utilized |
| Trehalose | utilized |
| Control | not utilized |

4. Cell Components

The cell wall of strain SANK 62585 was analyzed by the method of B. Becker et al [Applied Microbiology 12, 421–423 (1964)]. Since L,L-diaminopimelic acid and glycine were identified in the cell walls of all strains, the cell walls were considered to be of type I. The sugar components of the whole cells of the microorganisms were determined by the method of M. P. Lechevalier [Journal of Laboratory and Clinical Medicine 71, 934 (1968)]. No characteristic pattern could be observed.

EP 215,665 and U.S. Ser. No. 06/906,034 do not give the species for the strain SANK 62585. Further review in accordance with the usual standards [the ISP (The International Streptomyces Project); Bergey's Manual of Determinative Bacteriology, Eighth Edition; The Actinomycetes by S. A. Waksman; and other recent references on Actinomycetes] showed that the morphological and physiological properties were substantially identical with those of *Streptomyces carbophilus.*

For these reasons, Streptomyces strain SANK 62585 which produces the cytochrome P450 enzymes has been identified as *Streptomyces carbophilus* SANK 62585. As mentioned, this strain has been deposited in accordance with the provision of the Budapest Treaty on Aug. 13, 1985 at the Fermentation Research Institute, Japan, and given the accession number FERM BP-1145. Samples of the strain are available under the relevant provisions of the Budapest Treaty.

Actinomycetes including *Streptomyces carbophilus* SANK 62585 readily undergo mutation both through natural causes and as a result of artificial treatments such as UV irradiation, radiation treatment and chemical treatment. The present invention embraces all productive mutants of strain SANK 62585. These mutant strains also include any strains obtained by gene manipulation such as gene recombination, transduction and transformation. It is also well-known that the properties of Actinomycetes change in some degree even for the same strain after successive cultures. Therefore, strains cannot always be differentiated taxonomically because of a slight difference in culture properties.

This invention embraces all strains that can produce one or more of the cytochromes P-450 enzymes, and especially strains that cannot be clearly differentiated from strain SANK 62585 or its mutants.

Culture of the *Streptomyces carbophilus* strain 62585 to produce the P-450 enzymes is suitably performed by seeding of a conventional culture medium containing nutrients well-known for use with such microorganisms. Thus, the culture medium contains sources of assimilable carbon and of assimilable nitrogen and often contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulphate. If required, inorganic salts, such as sodium chloride, potassium chloride, calcium carbonate and various phosphates, may also be included. The medium is usually sterilized and has a pH adjusted to 5 to 8.

The particular cultivation technique employed is not critical to the invention and any technique commonly used for the cultivation of Streptomyces may equally be employed with the present invention. In general the techniques employed will be chosen having regard to industrial efficiency. Thus, liquid culture is generally preferred and the submerged culture method is most convenient from the industrial point of view. Cultivation is preferably carried out under aerobic conditions.

The enzymes of this invention are inducible enzymes, and are not produced unless an induction agent is present. For preference, the induction agent is selected to be the same as the intended substrate for the isolated enzyme. When from 4 hours to 3 days have elapsed after inoculation, preferably 1 to 5 mM, more preferably 2 mM of induction agent is added, and then cultivation is continued for 2 hours to 1 week, preferably for about one day. The temperature of cultivation is typically 20° to 45° C., preferably 25° to 30° C., optimally about 28° C. Shake culture or aeration techniques can be adopted.

The cells obtained by the cultivation may be disrupted by ultrasonication in buffer solution, and then the supernatant obtained by centrifugation gives a crude enzyme solution. The enzymes of the present invention are present in the supernatant obtained by centrifugation at 105,000 g for 1 hour.

In order to obtain electrophoretically pure $P-450_{sca-1}$, $P-450_2$, $P-450_{sca-3}$, the crude enzyme solution obtained after disruption of the cells may be purified by dialysis, ion-exchange column chromatography, gel filtration, hydroxyapatite column chromatography, or a combination thereof.

An illustrative method of purification is presented in the following Table.

TABLE A

| | |
|---|---|
| Cultured broth | 5,000 ml |
| ↓ | |
| Harvesting of cells | 8,000 rpm, 15 minutes |
| ↓ | |
| Disruption of cells | Ultrasonication, 10 minutes |
| ↓ | |
| Recovery of supernatant | 14,000 rpm, 30 minutes |
| ↓ | |
| Dialysis | pH 7.4 with 0.1M Tris-hydrochloric acid buffer solution |
| ↓ | |
| DEAE Toyopearl (Trade name, Toyo Soda Industries Inc) column chromatography | 0 to 0.30M NaCl gradient, eluted at about 0.10M NaCl |
| ↓ | |
| DEAE Toyopearl column chromatography | 0 to 0.20M NaCl gradient, eluted at about 0.10M NaCl |
| ↓ | |
| Cellurofine (Trade name, Chisso Inc) column chromatography | |
| ↓ | |
| Dialysis | pH 7.4 using 0.01M phosphate buffer |
| ↓ | |
| Hydroxylapatite (Bio-Rad Inc) column chromatography | 0.01M to 0.20M phosphate buffer concentration-gradient |
| ↓ | |
| $P-450_{sca-1}$, $P-450_{sca-2}$, and $P-450_{sca-3}$ | |

In the hydroxylapatite chromatography using a concentration gradient of phosphate buffer, cytochrome $P-450_{sca-1}$ is eluted first (at about 0.06M phosphate buffer), cytochrome $P-450_{sca-2}$ is eluted second (at about 0.08M phosphate buffer), and cytochrome $P-450_{sca-3}$ is eluted third (at about 0.10M phosphate buffer).

Each purified cytochrome P-450 enzyme obtained in this way migrated as a single band towards the anode in SDS-polyacrylamide electrophoresis.

Cytochrome $P-450_{sca-1}$, cytochrome $P-450_{sca-2}$, and cytochrome $P-450_{sca-3}$, provided in accordance with the present invention are different from other cytochrome P-450 enzymes.

Each enzyme of the present invention has a molecular weight of 46,000±1,000, based on a measurement using SDS-polyacrylamide electrophoresis. The maximum UV absorption occurs at 417 nm. In a reduced CO versus reduced difference spectrum, cytochrome $P-450_{sca-1}$ has a maximum absorption at 449 nm, and cytochrome $P-450_{sca-2}$ and cytochrome $P-450_{sca-3}$ both have a maximum absorption at 448 nm.

Each enzyme has a unique amino acid composition. The following data is given:

| amino acid | residues per molecule | |
| --- | --- | --- |
| residues | P-450$_{sca-1}$ | p-450$_{sca-2}$ |
| Asx | 39.1 | 36.9 |
| Thr | 30.9 | 30.0 |
| Ser | 22.4 | 21.1 |
| Glx | 41.8 | 39.6 |
| Pro | 26.8 | 26.7 |
| Gly | 28.7 | 25.9 |
| Ala | 48.0 | 45.4 |
| Cys | 3.1 | 1.9 |
| Val | 31.4 | 30.0 |
| Met | 7.8 | 8.1 |
| Ile | 18.2 | 18.0 |
| Leu | 49.7 | 49.1 |
| Tyr | 4.9 | 5.0 |
| Phe | 15.2 | 15.0 |
| His | 13.6 | 13.8 |
| Lys | 9.0 | 8.4 |
| Arg | 34.0 | 34.2 |
| Trp | 1.0 | 1.1 |
| Total | 425.6 | 410.2 |

The enzymes of this invention are useful as hydroxylation enzymes. They can hydroxylate a variety of different compounds. Accordingly, the present invention further provides a process for hydroxylating a substrate which comprises using an enzyme of this invention to introduce one or more hydroxy groups.

Contact of the enzyme with the substrate is preferably effected in an aqueous medium, for example in a phosphate buffer solution at a pH value in the range of from 5 to 9, more preferably 6.5 to 8.0, most preferably around 7.4. The reaction temperature is preferably within the range from 20° to 45° C., more preferably from 25° to 30° C. The optimum temperature is about 30° C. The concentration of the substrate in the reaction medium is preferably within the range from 0.01 to 5.0% by weight. The time allowed for the reaction is normally from 1 minute to 5 days, more usually from 1 day to 5 days, although this may vary, depending upon the concentration of substrate in the reaction mixture, the reaction temperature, and other factors.

After completion of the conversion reaction, the hydroxylated compound can be isolated using conventional procedures, including, for instance, filtration, solvent extraction, chromatography, crystallization, and other isolation procedures. Such procedures will be selected having due regard to the identity of the product. Before, during or after the isolation, the product may be derivatized, as desired.

The present invention will be further illustrated with reference to two classes of substrates of markedly different structure, namely macrolide compounds such as milbemycins, and ML-236B compounds.

There are several classes of known compounds with a structure based on a 16-membered macrolide ring. They are obtained by fermentation of various microorganisms or semi-synthetically by chemical derivatization of such natural fermentation products, and exhibit acaricidal, insecticidal, anthelmintic and other antiparasitic activities. The milbemycins and avermectins are examples of two such classes of known compounds, but various other classes also exist and are identified by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for general use with such compounds.

In order to avoid confusion, reference in this patent specification will be made to names based on the hypothetical parent compound represented by formula (C):

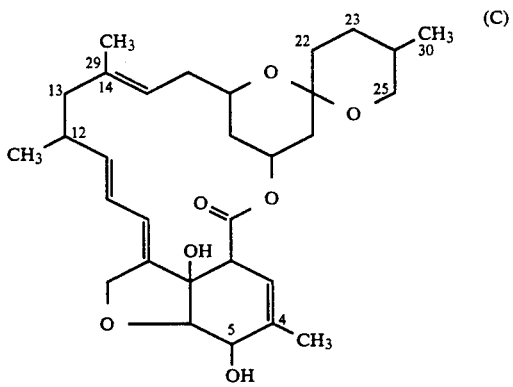

For the avoidance of doubt, formula (C) also shows the numbering of some carbon atoms most relevant to the compounds of the present invention. The methyl group at the 4-position has been numbered C-26.

The naturally produced milbemycins form a series of compounds. Milbemycins A$_3$ and A$_4$, among others, are disclosed in U.S. Pat. No. 3,950,360, and milbemycin D was disclosed in U.S. Pat. No. 4,346,171, though it was referred to as "Compound B-41D". These compounds may be represented by the above formula (C) in which position 25 is substituted respectively with a methyl group, an ethyl group or an isopropyl group. The milbemycin analogue substituted at position 25 with a sec-butyl is disclosed in U.S. Pat. No. 4,173,571.

13-Hydroxymilbemycins are disclosed in U.S. Pat. No. 4,093,629 and European Patent Specification 246,739. 13-hydroxy-5-ketomilbemycin derivatives are described in U.S. Pat. No. 4,423,209, also in European patent Specification 184,308 and Japanese Patent Application Kokai 108785 (1984). Milbemycin 5-oxime derivatives are disclosed in U.S. Pat. No. 4,547,520 and European Patent Specification 203,832. British Patent Specification 2,168,345 discloses milbemycin derivatives having a carboxy or esterified carboxy substituent at position 13 in combination with a hydroxy or esterified hydroxy substituent at position 5.

14-Hydroxymethylmilbemycin compounds can be prepared by oxidation of a 5-ketomilbemycin with selenium oxide/t-butylhydroperoxide, followed by reduction of the keto group at the position 5 with sodium borohydride, as described in J Am Chem Soc (1977) 99. 5526.

24-Hydroxymethylmilbemycin compounds can be prepared by microbial hydroxylation of a milbemycin compound using strains of *Amycolata autotrophica* which are deposited with the Fermentation Research Institute, Japan as FERM P-6181, FERM P-6182 and FERM P-6183. These deposited strains were named Nocardia sp SANK 62781, Nocardia sp SANK 62881 and Nocardia sp SANK 62981, respectively, at the time of the deposit. Their mycological properties are described in Japanese Patent Application Kokai 58-89191. As a result of a taxonomic review, the strains are currently placed in the genus Amycolata, independent of the genus Nocardia, because of differences in the cell wall composition [International Journal of Systematic Bacteriology (1986), 36, 29].

Like the milbemycins, the avermectins are based upon the same 16-membered macrolide ring compound. The avermectins were disclosed, for example in J Antimicrob Agents Chemother, 1979, 15, 361 (1979) and J Am Chem Soc, 1981, 103, 4216. These compounds may be represented by the above formula (C) but with position 13 substituted with a 4'-(α-L-oleandrosyl)-α-L-oleandrosyloxy group. Position 25 may be substituted with an isopropyl group or a sec-butyl group, and either there is a carbon-carbon double bond between positions 22 and 23, or there is a hydroxy group at position 23.

The avermectins are defined as follows:

| avermectin | $C_{22}-C_{23}$ | $R_{25}$ | $R_{23}$ | $R_5$ |
|---|---|---|---|---|
| $A_1a$ | db | sec-Bu | H | OMe |
| $A_1b$ | db | i-Pr | H | OMe |
| $A_2a$ | sb | sec-Bu | OH | OMe |
| $A_2b$ | sb | i-Pr | OH | OMe |
| $B_1a$ | db | sec-Bu | H | OH |
| $B_1b$ | db | i-Pr | H | OH |
| $B_2a$ | sb | sec-Bu | OH | OH |
| $B_2b$ | sb | i-Pr | OH | OH |

In the above table only, $R_{25}$ is a substituent at the 25 position; $R_{23}$ is a substituent at the 23 position; and $R_5$ is a substituent at the 5 position; "db" indicates a double bond between positions 22 and 23; and "sb" indicates a single bond between positions 22 and 23.

The 23-keto derivatives of avermectin $A_2a$, $A_2b$, $B_2a$ and $B_2b$ are known from U.S. Pat. No. 4,289,760. 22,23-Dihydroavermectins may be obtained by reduction of the double bond between the 22 and 23 positions and were disclosed in U.S. Pat. No. 4,199,569. The aglyclone derivatives of the avermectins, which are 13-hydroxymilbemycin analogues, have been reported in the literature. They have sometimes been referred to as C-076 compounds. Various derivatives are known: for example, U.S. Pat. No. 4,201,861 discloses such derivatives substituted with a lower alkanoyl group at position 13.

European Patent Specification 170,006 discloses a family of bioactive compounds produced by fermentation, identified collectively by the code number LL-F28249. Some of these have a 16-membered macrolide structure corresponding to the above formula (C), substituted with hydroxy at position 23 and with a 1-methyl-1-propenyl, 1-methyl-1-butenyl or 1,3-dimethyl-1-butenyl at position 25. In these compounds, the hydroxy at position 5 may also be replaced by methoxy.

The same or similar compounds identified as S-541 compounds are known from British Patent Specification 2,166,436. The 23-keto derivatives and 23-deoxy derivatives of S-541 are known from Belgian Patent 904,709. S-541 derivatives with a carbon-carbon double bond at positions 22 and 23 were disclosed in European Patent Specification 215,654. The 26-hydroxy and 26-$C_{1-4}$ alkanoyloxy derivatives of S-541 and of the 23-keto and 23-deoxy derivatives of S-541 are known from European Patent Specification 237,341.

British Patent Specification 2,176,182 discloses another group of macrolide antibiotics corresponding to the above formula (C), with a hydroxy or substituted hydroxy group at position 5, a hydroxy, substituted hydroxy or keto group at position 23, and an α-branched alkenyl group at position 25.

A yet further group of related macrolide derivatives was disclosed in Japanese Patent Application Kokai 62-29590. These have a structure corresponding to the above formula (C), with a hydroxy or methoxy group at position 5. Position 13 of the ring can be substituted with a 4'-(α-L-oleandrosyl)-α-L-oleandrosyloxy group, as in the avermectins, and there may be a carbon-carbon double bond between positions 22 and 23, or alternatively position 23 may be substituted with a hydroxy group. The substituent at position 25 is of a type not found in the naturally produced milbemycins and avermectins, and includes various α-branched alkyl, alkenyl, alkynyl, alkoxyalkyl, alkylthioalkyl and cycloalkylalkyl groups, or cycloalkyl, cycloalkenyl or heterocyclic groups. This 25-substituent is introduced by adding the corresponding carboxylic acid or derivative thereof to the fermentation broth of an avermectin-producing micro-organism.

The various classes of milbemycin-related macrolide compounds described above are all said to have one or more types of activity as antibiotic, anthelmintic, ectoparasiticidal, acaricidal or other pesticidal agents. However, there is still a continuing need to provide such macrolide compounds with modified activity against one or more classes of parasites. There is also a continuing need to develope improved routes to the known compounds.

Using the enzymes of this invention, new hydroxylated macrolide compounds can be obtained. Furthermore, known hydroxylated macrolides can be prepared.

To these ends, the present invention embraces a process for preparing a macrolide compound of formula (I):

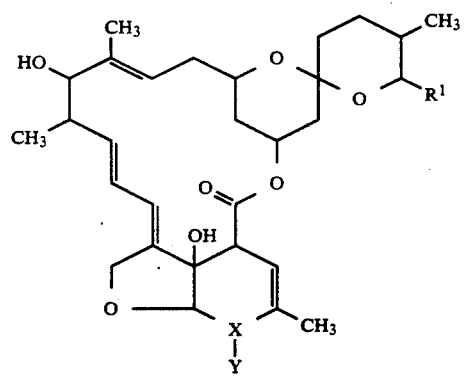

wherein $R^1$ represents a methyl group, an ethyl group, an isopropyl group, a sec-butyl group or a group of formula $-C(CH_3)=CHR^5$ in which $R^5$ represents a methyl group, an ethyl group or an isopropyl group, provided that when $R^1$ is a hydroxy group, then $R^3$ represents a methyl group, an ethyl group, an isopropyl group, or a sec-butyl group; and X(—4) represents CHOH or C(=N—OH).

The process for preparing the macrolide compounds (I) involves enzymatic hydroxylation of a compound of formula (II):

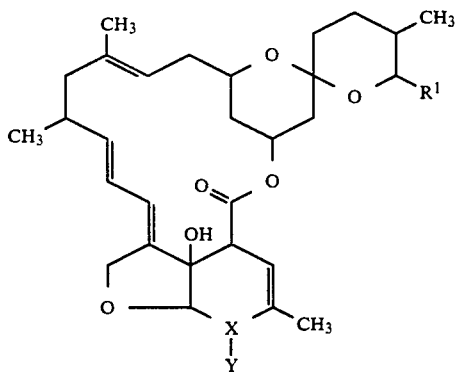

wherein R¹ and —X(—Y)— are as defined above) using an enzyme of this invention.

The starting materials of formula (II) are known compounds or may be prepared by methods described in the literature on macrolides mentioned above, incorporated herein by reference. Naturally occurring milbemycins of formula (II) are formed by fermentation, and often occur as mixtures. Such mixtures can be separated before reaction, or used as such.

After completion of the conversion reaction, the desired compound can be obtained from the reaction system, collected, isolated and purified by conventional means. For example, the reaction product is filtered and the filtrate is extracted with a water-immiscible organic solvent such as ethyl acetate. After evaporation of the solvent of the extract, the remaining crude hydroxylated macrolide compound may be purified by subjecting it to column chromatography using silica gel or alumina, and by eluting with a suitable eluent. If the starting material is a mixture, then the product can be isolated as a mixture of hydroxylated compounds which if desired can be separated using chromatography or other suitable techniques.

In general, the compounds of formula (I) have parasiticidal activity, embracing insecticidal, acaricidal and anthelmintic activities, and/or are useful as intermediates for synthesis of other compounds, particularly 13-esterified derivatives having different insecticidal, acaricidal and anthelmintic activities.

In particular, the compounds (I) have acaricidal activity against adults, larvae and eggs of Tetranychus, Panonychus and rust mites which are parasitic on fruit trees, vegetables and flowering plants, and against Ixodidae, Dermanyssidae, Sarcoptidae and so on which are parasitic on animals.

They also have activity against Oestrus, Lucilia, Hypoderma, Gautrophilus and so on: fleas, lice and so on which are ectoparasitic on animals and birds; domestic insects such as cockroaches, houseflies and so on; and various harmful insects on agriculture and horticulture such as aphids and larvae of Lepidoptera. Furthermore, they are active against Meloidogyne in soil, Bursaphelenchus, Rhizoglyphus and so on.

The compounds (I) also have activity against insects harmful to plants, particularly insects such as phytophagous insects.

In addition, the compounds (I) have parasiticidal activity and may be used as an anthelmintic agent for animals and humans. They are effective particularly against nematodes parasitic on domestic animals and poultry and pets such as pigs, sheep, goats, cattle, horses, dogs, cats and fowl.

For agricultural and horticultural purposes, the compounds (I) can be made into various kinds of formulation already known in these fields, such as powders, wettable powders, emulsifiable concentrates and so on. Such formulations may be diluted with water to a concentration of active ingredient of 1 to 10 ppm.

For use as a anthelmintic agent for animals, the compounds (I) can be made into various forms of preparation already known in this field, such as powders, tablets, capsules and injections. When they are orally administered, a dose of 0.01 to 100 mg, preferably 0.5 to 50 mg, of the ingredient per 1 kg of body weight is preferred.

The other illustrative use of the hydroxylation enzymes of this invention is in the hydroxylation of ML-236B compounds.

In U.S. Pat. No. 4,346,227, there is described the enzymatic hydroxylation of a compound ML-236B, or ML-236B carboxylic acid or a salt or ester thereof. ML-236B is a lactone of the structure (D):

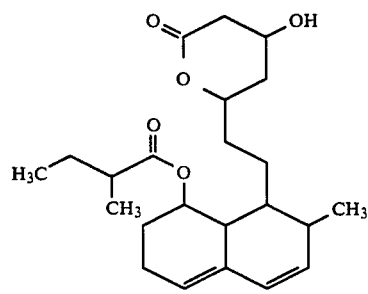

and can exist in a ring-open form as a carboxylic acid of the structure (E):

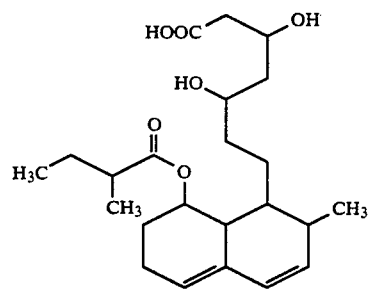

Hydroxylation typically gives a mixture of two compounds, with the product of interest (in lactone form) being of the structure (F):

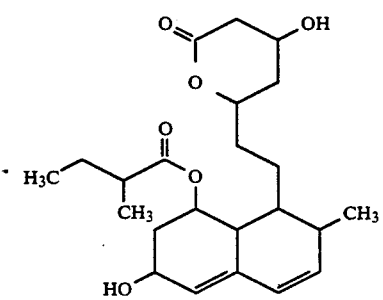

In U.S. Pat. No. 4,346,227, this compound is called M-4 lactone. The sodium salt of M-4 is now known as pravastatin sodium. Thus, the sodium salt of the 6β-hydroxy derivative of ML-236B carboxylic acid is pravastatin sodium.

Each enzyme of this invention hydroxylates at least the 6 position of ML-236B compounds in the presence of ferredoxin, ferredoxin-NADP+-reductase, NADPH and dissolved oxygen, in accordance with the following scheme:

pH value of the reaction mixture, in a way which is predictable by ordinary laws of chemistry. The starting material and the other factors are preferably chosen so as to facilitate production of pravastatin sodium.

Of the ML-236B compounds used as starting materials, the alkali metal salts, e.g. the sodium or potassium salts, are particularly preferred, the sodium salt being most preferred, as this gives the best conversion of starting compound into the desired hydroxylated compound pravastatin sodium.

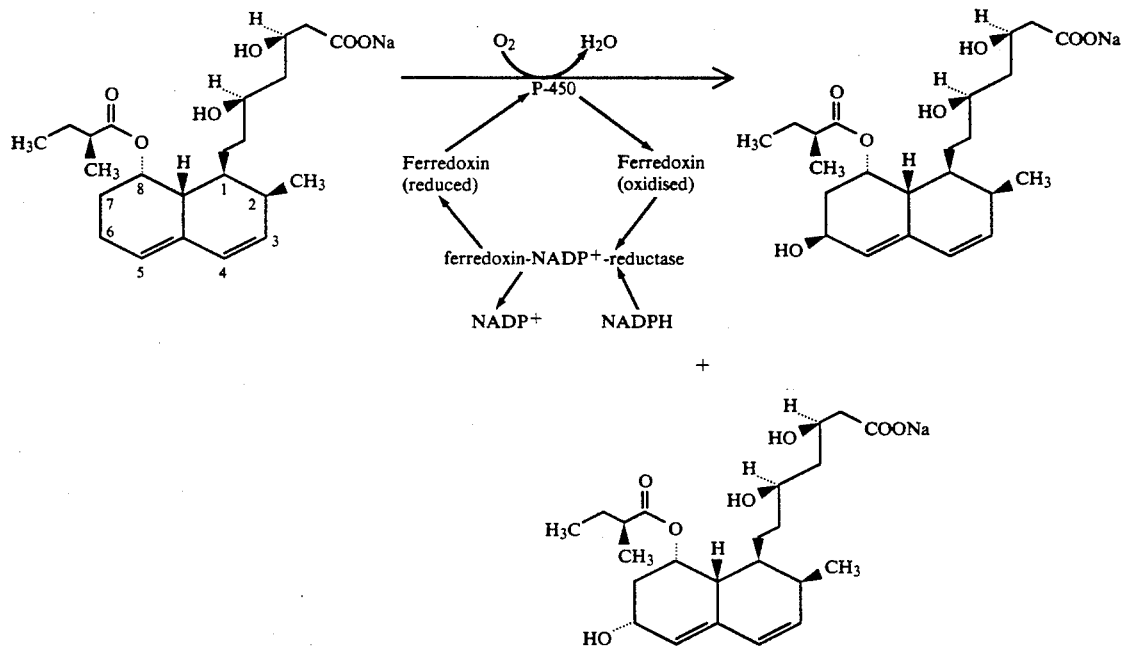

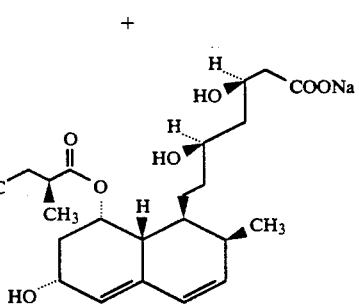

Thus, for example, sodium 6β-hydroxy-ML-236B carboxylate is isolated as the main product, along with sodium 6α-hydroxy-ML-236B carboxylate as by-product.

When each cytochrome P-450 enzyme of this invention is reacted with sodium ML-236B carboxylate as substrate at pH 7.4 for 5 minutes with (a) ferredoxin, (b) ferredoxin-NADP+-reductase, (c) NADP+, (d) NADPH regeneration system, and (e) dissolved oxygen, the temperature of action ranges at least from 4° C. to 60° C. The optimum pH for each cytochrome ranges from 6.5 to 8.0. Each cytochrome is stable when kept for 24 hours at 4° C. in the pH range between 6.0 and 9.0.

The use of ferredoxin, ferredoxin-NADP+-reductase, oxygen and NADPH is not essential. Any components which can activate the cytochrome P-450 may be adopted.

Furthermore, the substrate is not limited to the sodium salt of ML-236 carboxylic acid. The ML-236B starting compound may be the free carboxylic acid, its corresponding lactone or a salt thereof (e.g. a metal, amino acid or amine salt). The cytochrome P-450 enzyme of the invention has no effect in itself on the carboxy group of the ML-236B compound. Hence, other factors being equal, ML-236B lactone gives a hydroxy ML-236B lactone, ML-236B carboxylic acid gives a hydroxy ML-236B carboxylic acid and a salt of ML-236B carboxylic acid gives the same salt of the hydroxy ML-236B carboxylic acid. However, the identity of the product may be affected by other factors, especially the The cytochrome P-450 enzyme of this invention used for hydroxylation of a ML-236B compound as substrate is preferably one produced from *Streptomyces carbophilus* SANK 62585 using a ML 236B compound as an induction agent, especially sodium ML-236B carboxylate.

Measurement of the enzyme activity is normally effected in one of two ways:

(i) Measurement on cytochrome P-450$_{sca-1}$, cytochrome P-450$_{sca-2}$, and cytochrome P-450$_{sca-3}$ Measurement is performed according to the method of Omura and Sato et al. (J Biol Chem, 239. 1964, 2370). That is to say, cytochrome P-450$_{sca-1}$, cytochrome P-450$_{sca-2}$, and cytochrome P-450$_{sca-3}$ are analyzed quantitatively using the following formula, based on the difference in the absorbance of the reduced CO versus the reduced difference spectrum at 450 nm and 490 nm.

*cytochrome P-450 (nmol/ml) = (O.D. 450 nm − O.D. 490 nm) × 1.000/91 (nmol/ml)*

(ii) Measurement of rate of formation of pravastatin sodium from sodium ML-236B carboxylate The following cocktail of components is employed:

| | |
|---|---|
| Enzyme solution containing P-450 | 0.14 ml |
| NADPH regeneration system: | |
| NADP+ | 0.26 mM |
| Glucose-6-phosphate | 14.0 mM |
| Glucose-6-phosphate dehydrogenase | 0.2 unit |
| Nicotinamide | 10.0 mM |

-continued

| | |
|---|---|
| MgCl$_2$ | 2.5 mM |
| Ferredoxin-NADP$^+$-reductase (spinach) | 0.04 unit |
| Ferredoxin (spinach) | 320.0 μg |
| Sodium ML-236B carboxylate | 0.233 mM |
| Total volume | 0.20 ml |

The components of the Table are mixed, the solution is shaken at 30° C. for 5 minutes, and then 10 μl of 6N NaOH is added and the reaction stopped. The amount of pravastatin sodium formed by the enzyme system is determined with HPLC.

Using the test methods for determining activity, the loss of activity with change in temperature and pH can be determined.

For example, each cytochrome is fully inactivated at pH 7.4 and 70° C. for 60 minutes in the presence of 20% glycerol and 2 mM dithiothreitol. Each cytochrome is inactivated at pH 3 or a more acidic pH, and at pH 11 or a more basic pH (when treated at 4° C. for 24 hours in the presence of 20% glycerol and 2 mM dithiothreitol).

The effects of potential inhibitors against cytochrome P-450$_{sca-1}$ P-450$_{sca-2}$, P-450$_{sca-3}$ and the effects of metallic ions on the action of the cytochrome P-450 can be assessed quantitatively using the method (ii).

The following results are typically obtained.

| | Residual activity of enzyme | | |
|---|---|---|---|
| Added compound | P-450$_{sca-1}$ | P-450$_{sca-2}$ | P-450$_{sca-3}$ |
| 1 mM CoCl$_2$ | 65.0% | 67.5% | 60.1% |
| 1 mM MnCl$_2$ | 20.0% | 18.7% | 17.5% |
| 1 mM CuCl$_2$ | 0% | 0% | 0% |
| 1 mM CaCl$_2$ | 100.0% | 100.0% | 100.0% |
| 2 mM SKF-525A* | 25.8% | 22.8% | 24.1% |
| 2 mM Cimetidine | 58.7% | 45.7% | 43.8% |
| CO bubbled in for 1 minute | 50.0% | 55.0% | 60.4% |

*SKF-525A: 2-diethylaminoethyl-2,2-diphenyl valerate hydrochloride

Each cytochrome was inhibited by Co$^{2+}$, Mn$^{2+}$, and Cu$^{2+}$. Each cytochrome was also inhibited by the typical inhibitors of cytochrome P-450 enzymes, such as SKF-525A (2-diethylaminoethyl-2,2-diphenyl valerate hydrochloride), cimetidine, and carbon monoxide.

EXAMPLES OF THE INVENTION

The present invention is illustrated by the following non-limiting examples.

EXAMPLE 1

A culture medium containing 2% glucose, 1% peptone and 0.1% yeast extract was prepared and adjusted to pH 7.0. Ten Erlenmeyer flasks of 100 ml volume, each of which contained 20 ml of the medium, were sterilized at 121° C. for 15 minutes. Each flask was then inoculated with a platinum loop of *Streptomyces carbophilus* SANK 62585 (FERM BP-1145), and then culture with shaking at 220 rpm was continued at 28° C. for 3 days, giving a seed culture.

100 ml aliquots of the medium were poured into 500 ml Erlenmeyer flasks, and sterilized at 121° C. for 15 minutes. 0.5 ml of seed culture was added into each 500 ml flask, and full-scale culture of 50 flasks was performed. After one day of full-scale culture, sodium ML-236B carboxylate was added into each flask to a level of 0.1%, and further culture was continued for one day.

After culture, the cells were collected by centrifugation, giving 190 g of cells. The mass of cells was suspended in twice its volume of 80 mM Tris-hydrochloric acid buffer solution which contained 2 mM dithiothreitol and 20% glycerin, and then the cells ruptured with ultrasonication. A crude enzyme solution was obtained as a supernatant by centrifugal separation.

From the crude enzyme solution, cytochrome P-450$_{sca-1}$, cytochrome P-450$_{sca-2}$, and cytochrome P-450$_{sca-3}$ were purified according to the process presented in the preceding Table A. After dialysis of the crude enzyme solution, DEAE Toyopearl chromatography was performed twice, and then gel filtration chromatography was carried out with Cellurofine. Lastly, hydroxylapatite chromatography was performed, and the enzymes were eluted with phosphate buffer. Cytochrome P-450$_{sca-1}$ was eluted with about 0.06M phosphate buffer, cytochrome P-450$_{sca-2}$ was eluted with about 0.08M phosphate buffer, and cytochrome P-450$_{sca-3}$ was eluted with about 0.10M phosphate buffer. Each enzyme was obtained as an electrophoretically pure P-450. The results of the purification are presented in the following Table.

| Purification step | Total protein (mg) | Total P450 (nmol) | P-450/protein (nmol/mg) | Recovery of P-450 (%) |
|---|---|---|---|---|
| Crude enzyme solution | 34268.0 | 1439 | 0.04 | 100.0 |
| DEAE Toyopearl 650 S | 660.1 | 1439 | 2.18 | 100.0 |
| DEAE Toyopearl 650 S | 55.3 | 466 | 8.43 | 32.4 |
| Cellurofine GCL 2000 m | 27.7 | 302 | 10.90 | 21.0 |
| Hydroxylapatite* | | | | |
| P-450$_{sca-1}$ | 8.4 | 110 | 13.05 | 7.6 |
| P 450$_{sca-2}$ | 9.5 | 121 | 12.74 | 8.4 |
| P-450$_{sca-3}$ | 1.9 | 24.1 | 12.80 | 1.7 |

*Hydroxylapatite: DNA-Grade Bio-gel HTP

Amino acid analysis was then performed.

The amino acids except for Cys and Trp were produced by hydrolysis with 6N HCl at 110° C. for 24 hours by the method described in J. W. Eveleigh and G. D. Winter (1970) protein Sequence Determination. Ed S. B. Needleman, Springer-Verlag, 92.

The amino acid Cys was assayed using oxidation with H$_2$O$_2$/HCOOH and subsequent hydrolysis with HCl to give cysteic acid, in accordance with the method described by E. Schrau et al. Biochem J, (1954) 57, 33. More specifically, 80 μl of sample solution was dissolved in 100 ul of 99% formic acid and 20 μl of methanol. Meanwhile, 10 μl of H$_2$O$_2$ and 190 μl of 99% formic acid were maintained in a sealed tube at 25° C. for 2 hours. Both solutions were cooled at −10° C. for 30 minutes and then mixed. The mixture was kept at −10° C. for 2.5 hours, then 160 μl of the reaction mixture was evaporated to dryness and lyophilized. The lyophilized sample was then subjected to hydrolysis with 6N HCl at 110° C. for 24 hours, in the same way as for other amino acids.

The amino acid Trp was produced by hydrolysis with 3N mercaptoethanesulfonic acid at 110° C. for 24 hours by the method described by B. Penke et al. in Anal Biochem (1974) 60, 45.

The assay was performed with a Hitachi Amino Acid Analyzer Model 835.

The following data was obtained:

| amino acid residue | amino acid data residues per molecule | |
|---|---|---|
| | P-450$_{sca-1}$ | p-450$_{sca-2}$ |
| Asx | 39.1 | 36.9 |
| Thr | 30.9 | 30.0 |
| Ser | 22.4 | 21.1 |
| Glx | 41.8 | 39.6 |
| Pro | 26.8 | 26.7 |
| Gly | 28.7 | 25.9 |
| Ala | 48.0 | 45.4 |
| Cys | 3.1 | 1.9 |
| Val | 31.4 | 30.0 |
| Met | 7.8 | 8.1 |
| Ile | 18.2 | 18.0 |
| Leu | 49.7 | 49.1 |
| Tyr | 4.9 | 5.0 |
| Phe | 15.2 | 15.0 |
| His | 13.6 | 13.8 |
| Lys | 9.0 | 8.4 |
| Arg | 34.0 | 34.2 |
| Trp | 1.0 | 1.1 |
| Total | 425.6 | 410.2 |

Errors in the analysis are believed to be a range of about plus/minus 5% in the case of hydrolysis for 24 hours, provided that the specimen is reasonably pure. The error is reduced to about plus/minus 2% if hydrolysis is performed periodically, e.g. 24 hours, 48 hours, 72 hours, etc.

The reliability is governed by two factors. One is resistance to hydrolysis. It is empirically known that linkages such as Val-Val, Val-Gly, etc, are resistant to hydrolysis. Error caused by this factor may be minimized by prolonging the period of hydrolysis.

The other factor is the susceptibility of amino acids so produced to hydrolysis. For example, Ser and Thr are known to be sensitive to hydrolysis with HCl. Error can be increased by the prolonged hydrolysis period as far as these amino acids are concerned.

EXAMPLE 2

13-hydroxymilbemycin A$_4$

Reaction was effected at 30° C. for one hour, using milbemycin A$_4$ as substrate, according to the following mix:

| P-450 (purified enzyme) | see below |
|---|---|
| NADPH regenerating system | |
| NADP$^+$ | 0.26 mM |
| glucose-6-phosphate | 14.0 mM |
| glucose-6-phosphate dehydrogenase | 0.2 unit |
| nicotinamide | 10.0 mM |
| MgCl$_2$ | 2.5 mM |
| Ferredoxin-NADP$^+$-reductase (spinach) | 0.04 unit |
| Ferredoxin (spinach) | 320.0 μg |
| Milbemycin A$_4$ | 0.92 mM |
| 1,4-dioxane | 1.0 μl |
| Total volume | 0.2 ml |

The quantity of P-450 was 0.431 nmol in the case of P-450$_{sca-1}$, 0.646 nmol in the case of P-450$_{sca-2}$, and 0.188 nmol in the case of P-450$_{sca-3}$.

The results are presented in the following Table.

| | 13-hydroxymilbemycin A$_4$ (μg/ml) |
|---|---|
| P-450$_{sca-1}$ system | 3.605 |
| P-450$_{sca-2}$ system | 5.035 |
| P-450$_{sca-3}$ system | 2.451 |
| System without P-450 enzyme | 0 |

HPLC data was as follows:
column: Senshu Pack ODS-1251-P (4.6 mm×250 mm)
solvent: 65% acetonitrile
flow rate: 5 μl
detector: UV 240 nm
retention time: 4.97 minute The mass spectrum coincided with that for an authentic sample.

EXAMPLE 3

13-hydroxy-5-ketomilbemycin A$_4$ 5-oxime

The procedure of Example 2 was repeated using 5-ketomilbemycin A$_4$ 5-oxime as a substrate, giving 13-hydroxy-5-ketomilbemycin A$_4$ 5-oxime.

HPLC data was as follows:
column: Senshu Pack ODS-1251-P (4.6 mm×250 mm)
solvent: 65% acetonitrile
flow rate: 5 μl
detector: UV 240 nm
retention time: 5.747 minute The mass spectrum coincided with that for an authentic sample.

EXAMPLE 4

Pravastatin Sodium

Reaction was effected at 30° C. for one hour, using sodium ML-236B carboxylate as a substrate in the following mix:

| P-450 (the purified sample) | see below |
|---|---|
| NADPH regeneration system | |
| NADP$^+$ | 0.26 mM |
| glucose-6-phosphate | 14.0 mM |
| glucose-6-phosphate dehydrogenase | 0.2 unit |
| nicotinamide | 10.0 mM |
| MgCl$_2$ | 2.5 mM |
| Ferredoxin-NADP$^+$-reductase (spinach) | 0.04 unit |
| Ferredoxin (spinach) | 320.0 μg |
| Sodium ML-236B carboxylate | 2.3 mM |
| Total | 0.2 ml |

The quantity of P-450 was 0.862 nmol in the case of P-450$_{sca-1}$, 1.292 nmol in the case of P-450$_{sca-2}$, and 0.377 nmol in the case of P-450$_{sca-3}$.

The results are presented in the following Table.

| | pravastatin Na (μg/ml) | Na 6α-hydroxy-ML-236B carboxylate (μg/ml) |
|---|---|---|
| P-450$_{sca-1}$ system | 29.4 | 2.9 |
| P-450$_{sca-2}$ system | 50.3 | 6.3 |
| P-450$_{sca-3}$ system | 17.11 | 2.99 |
| System without P-450 enzyme | 0 | 0 |

HPLC data was as follows:
column: Radial-PAK cartridge C$_{18}$ (5.0 mm×100 mm)
solvent: 27% acetonitrile/0.1% triethylamine-Phosphoric acid (pH 3.2)
flow rate: 5 μl
detector: UV 240 nm
retention time: 10.89 minute The mass spectrum coincided with that for an authentic sample.

The results show that Pravastatin sodium has been prepared with high selectivity from sodium ML-236B carboxylate.

The spinach ferredoxin may be replaced by ferredoxin from *Chlostridium pasteurianum*.

We claim:

1. A soluble hydroxylation enzyme selected from the group consisting of cytochrome P-450$_{sca\text{-}1}$, cytochrome P-450$_{sca\text{-}2}$ and cytochrome P-450$_{sca\text{-}3}$, wherein
   (a) the enzymes have a molecular weight of 46,000±1,000 daltons as determined by SCS-polyacrylamide gel electrophoresis,
   (b) by hydroxyapatite chromatography, cytochrome P-450$_{sca\text{-}1}$ is eluted with about 0.06M phosphate buffer, cytochrome P-450$_{sca\text{-}2}$ is eluted with about 0.08M phosphate buffer, and cytochrome P-450$_{sca\text{-}3}$ is eluted with about 0.10M phosphate buffer,
   (c) the enzymes are capable of hydroxylating ML-236B and milbemycin as substrates, said ML-236B being a lactone of the formula

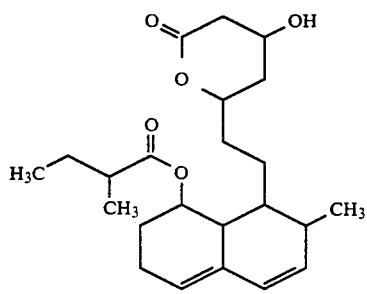

or in a ring-open form as a carboxylic acid of the formula

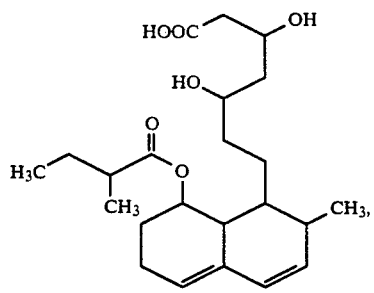

and
   (d) the enzymes are capable of being induced by ML-236B as an induction agent.

2. The hydroxylation enzyme according to claim 1, wherein the enzyme is cytochrome P-450$_{sca\text{-}1}$.

3. The hydroxylation enzyme according to claim 1, wherein the enzyme is cytochrome P-450$_{sca\text{-}2}$.

4. The hydroxylation enzyme according to claim 1, wherein the enzyme is cytochrome P-450$_{sca\text{-}3}$.

5. The hydroxylation enzyme according to claim 1, wherein the enzyme is cytochrome P-450$_{sca\text{-}1}$ and said cytochrome P-450$_{sca\text{-}1}$ has the following amino acid composition in terms of residues per molecule:

| | |
|---|---|
| Asx | 39.1 |
| Thr | 30.9 |
| Ser | 22.4 |
| Glx | 41.8 |
| Pro | 26.8 |
| Gly | 28.7 |
| Ala | 48.0 |
| Cys | 3.1 |
| Val | 31.4 |
| Met | 7.8 |
| Ile | 18.2 |
| Leu | 49.7 |
| Tyr | 4.9 |
| Phe | 15.2 |
| His | 13.6 |
| Lys | 9.0 |
| Arg | 34.0 |
| Trp | 1.0 |
| Total | 425.6 |

6. The hydroxylation enzyme according to claim 1, wherein the enzyme cytochrome is P-450$_{sca\text{-}2}$ and said cytochrome P-450$_{sca\text{-}2}$ has the following amino acid composition in terms of residues per molecule:

| | |
|---|---|
| Asx | 36.9 |
| Thr | 30.0 |
| Ser | 21.1 |
| Glx | 39.6 |
| Pro | 26.7 |
| Gly | 25.9 |
| Ala | 45.4 |
| Cys | 1.9 |
| Val | 30.0 |
| Met | 8.1 |
| Ile | 18.0 |
| Leu | 49.1 |
| Tyr | 5.0 |
| Phe | 15.0 |
| His | 13.8 |
| Lys | 8.4 |
| Arg | 34.2 |
| Trp | 1.1 |
| Total | 410.2 |

7. The hydroxylation enzyme according to claim 1, wherein the enzyme is cytochrome P-450$_{sca\text{-}1}$ and said cytochrome P-450$_{sca\text{-}1}$ has a maximum absorption at 449 based on the difference in absorbance of the reduced CO versus reduced difference spectrum at 450 nm and 490 nm.

8. The hydroxylation enzyme according to claim 1, wherein the enzyme is cytochrome P-450$_{sca\text{-}2}$ and said cytochrome P-450$_{sca\text{-}2}$ has a maximum absorption at 448 nm based on the difference in absorbance of the reduced CO versus reduced difference spectrum at 450 nm and 490 nm.

9. The hydroxylation enzyme according to claim 1, wherein the enzyme is cytochrome P-450$_{sca\text{-}3}$ and said cytochrome P-450$_{sca\text{-}3}$ has a maximum absorption at 448 nm based on the difference in absorbance of the reduced CO versus reduced difference spectrum at 450 nm and 490 nm.

10. The hydroxylation enzyme according to claim 1, wherein the enzyme is produced by the isolated from *Streptomyces carbophilus* SANK 62585.

11. The hydroxylation enzyme according to claim 1, wherein the enzyme is obtained as a soluble fraction supernatant from a centrifugal separation.

12. A method for producing a hydroxylation enzyme selected from the group consisting of cytochrome P-450$_{sca\text{-}1}$, cytochrome P-450$_{sca\text{-}2}$ and cytochrome P-450$_{sca\text{-}3}$, which method comprises culturing *Streptomy-* ces carbophilus SANK 62585 in a cultivation medium, adding to said cultivation medium an induction agent capable of inducing production of said enzyme, further culturing said Streptomyces carbophilus SANK 62585, and isolating said hydroxylation enzyme by hydroxyapatite chromatography, wherein cytochrome P-450$_{sca-1}$ is eluted with about 0.06M phosphate buffer, cytochrome P-450$_{sca-2}$ is eluted with about 0.08M phosphate buffer, and cytochrome P-450$_{sca-3}$ is eluted with about 0.10M phosphate buffer.

13. In a process for the hydroxylation of a substrate using an enzyme, the improvement which comprises using as said enzyme a cytochrome P-450 enzyme produced by and isolated from Streptomyces carbophilus SANK 62585,
wherein said hydroxylation enzyme is selected from the group consisting of cytochrome P-450$_{sca-1}$, cytochrome P-450$_{sca-2}$ and cytochrome P-450$_{sca-3}$.

14. A hydroxylation process which comprises providing at least one hydroxylation enzyme selected from the group consisting of cytochrome P-450$_{sca-1}$, cytochrome P-450$_{sca-2}$ and cytochrome P-450$_{sca-3}$; providing a substrate for said enzyme; hydroxylating said substrate using said hydroxylation enzyme; and obtaining a hydroxylated substrate.

15. The process of claim 14, wherein said hydroxylation enzyme has been prepared by the steps of culturing Streptomyces carbophilus SANK 62585 in a cultivation medium, adding to said cultivation medium an induction agent capable of inducing production of said enzyme, further culturing said Streptomyces carbophilus SANK 62585, and isolating said hydroxylation enzyme.

16. The process of claim 15, wherein said induction agent and said substrate are the same compound.

17. The process of claim 15, wherein the isolating of said hydroxylation enzyme is conducted by hydroxyapatite chromatography, wherein cytochrome P-450$_{sca-1}$ is eluted with about 0.06M phosphate buffer, cytochrome P-450$_{sca-2}$ is eluted with about 0.08M phosphate buffer, and cytochrome P-450$_{sca-3}$ is eluted with about 0.10M phosphate buffer.

* * * * *

UNITED STATES PATENT AND TRADEMARK OFFICE
CERTIFICATE OF CORRECTION

PATENT NO. : 5,179,013
DATED : January 12, 1993
INVENTOR(S) : MATSUOKA et al It is certified that error appears in the above-identified patent and that said Letters Patent is hereby corrected as shown below:

Column 10, line 65, change "X(-4)" to --X(-Y)--.

Column 11, line 18, before "wherein", insert --(--.

Column 19, line 13 (claim 1), change "SCS-" to -- SDS- --.

Column 20, line 16 (claim 5), after "425.6" insert -- . --.

Column 20, line 19 (claim 6), change "enzyme cytochrome is" to -- enzyme is cytochrome --.

Column 20, line 39 (claim 6), after "410.2", insert -- . --.

Column 20, line 60 (claim 10), change "the isolated" to -- and isolated --.

Signed and Sealed this

Twenty-second Day of March, 1994

*Attest:*

BRUCE LEHMAN

*Attesting Officer*   *Commissioner of Patents and Trademarks*